United States Patent [19]

Luft et al.

[11] Patent Number: 4,965,234
[45] Date of Patent: Oct. 23, 1990

[54] SUPPORTED CATALYST FOR THE PREPARATION OF MONOCARBOXYLIC ANHYDRIDES

[75] Inventors: Gerhard Luft, Mühltal; Peter Trabold, Dieburg, both of Fed. Rep. of Germany

[73] Assignee: Hoechst Aktiengesellschaft, Hurth, Fed. Rep. of Germany

[21] Appl. No.: 319,138

[22] Filed: Mar. 3, 1989

[30] Foreign Application Priority Data

Mar. 17, 1988 [DE] Fed. Rep. of Germany ....... 3808868

[51] Int. Cl.$^5$ ............................................. B01J 31/00
[52] U.S. Cl. ................................... 502/154; 502/162; 502/166; 502/167; 502/168
[58] Field of Search ............... 502/154, 166, 162, 167, 502/168

[56] References Cited

U.S. PATENT DOCUMENTS

| | | | |
|---|---|---|---|
| 3,907,852 | 9/1975 | Oswald et al. | 502/162 |
| 4,542,119 | 9/1985 | Hsu et al. | 502/153 |
| 4,564,711 | 1/1986 | Hsu et al. | 502/153 |
| 4,657,884 | 4/1987 | Luft et al. | 502/161 |
| 4,668,795 | 5/1987 | Andrade et al. | 548/412 |

FOREIGN PATENT DOCUMENTS

| | | |
|---|---|---|
| 1167064 | 5/1984 | Canada. |
| 0079461 | 5/1983 | European Pat. Off.. |
| 0185882 | 7/1986 | European Pat. Off.. |
| 0245893 | 11/1987 | European Pat. Off.. |
| 0263564 | 4/1988 | European Pat. Off.. |
| 3440646 | 5/1986 | Fed. Rep. of Germany. |
| 2092017 | 8/1982 | United Kingdom. |

*Primary Examiner*—H. M. S. Sneed
*Assistant Examiner*—E. P. Irzinski
*Attorney, Agent, or Firm*—Connolly and Hutz

[57] ABSTRACT

In a supported catalyst for the preparation of monocarboxylic anhydrides by carbonylation of the appropriate esters or ethers, where, in the supported catalyst, an organosilicon compound is bonded, as a polyfunctional coupling agent, on the one hand to a support material and on the other hand to a noble-metal compound from group VIII of the Periodic Table of the Elements, the coupling agent is a chelate-forming organosilicon compound of the general formula

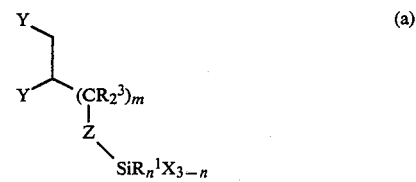

or

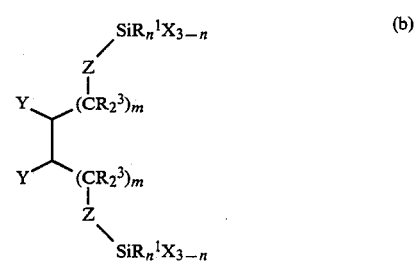

where
X=Cl, Br or —OR$^2$;
Y=—NR$_2^4$, a nitrogen-containing aryl radical, —PR$_2^4$, AsR$_2^4$, —SR$^4$ or —SH;
Z=zero, arylene or phenylene (optionally ortho-, meta- or para-substituted),
R$^1$=C$_1$ to C$_5$-alkyl;
R$^2$=C$_1$ to C$_5$-alkyl or —C$_6$H$_5$;
R$^3$=—H or C$_1$ to C$_3$-alkyl;
R$^4$=C$_1$ to C$_6$-alkyl, C$_5$ or C$_6$-cycloalkyl or —C$_6$H$_5$ or —CH$_2$C$_6$H$_5$, which are optionally substituted by halogen, methoxy, ethoxy or C$_1$ to C$_3$-alkyl groups;
n=0 or 1 or 2;
m=2 to 6, preferably 2 to 4.

9 Claims, No Drawings

SUPPORTED CATALYST FOR THE PREPARATION OF MONOCARBOXYLIC ANHYDRIDES

The invention relates to a supported catalyst for the preparation of monocarboxylic anhydrides by carbonylation of the appropriate esters or ethers, where, in the supported catalyst, an organosilicon compound containing alkoxy or halogen groups and containing organonitrogen, organophosphorus, organoarsenic, organosulfur or mercapto groups, is bonded, as a polyfunctional coupling agent, on the one hand to a support material and on the other hand to a noble-metal compound from group VIII of the Periodic Table of the Elements A supported catalyst of this type is known from German Offenlegungsschrift 3,440,646. In addition, German Offenlegungsschrift 3,511,048 A1 describes a supported catalyst in which the support material has simply been impregnated with the solution of a noble-metal chelate compound formed from the noble-metal compound and a chelating agent containing organonitrogen, organophosphorus, organoarsenic, organosulfur or mercapto groups.

The object of the present invention is to modify the chelating agent in a manner such that it acts as a polyfunctional coupling agent and that the service life (duration of activity) and selectivity of the supported catalyst clearly improve with the same support material. In particular, the supported catalyst according to the invention is intended for the preparation of monocarboxylic anhydrides of the general formula $(RCO)_2O$ by reacting a carboxylic acid ester or dialkyl ether of the general formula $RCOOR$ or $ROR$ respectively, where R in each case denotes the same alkyl radical having 1–4 carbon atoms, with carbon monoxide in the gas phase in the presence of iodine or bromine or compounds thereof as reaction promoter, at temperatures of from 130° to 400° C. and pressures of from 1–150 bar.

A process of this type which operates in the gas phase using a supported catalyst has already been disclosed in German Offenlegungsschrift 3,440,647, which avoids the disadvantages occurring in liquid-phase processes, for example the difficult separation and recycling of suspended and, in some cases, dissolved catalyst and, where appropriate, promoter.

In detail, the invention has the feature that the coupling agent is a chelate-forming organosilicon compound of the general formula

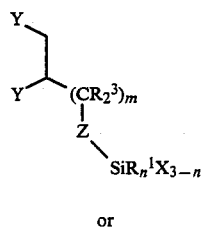

(a)

or

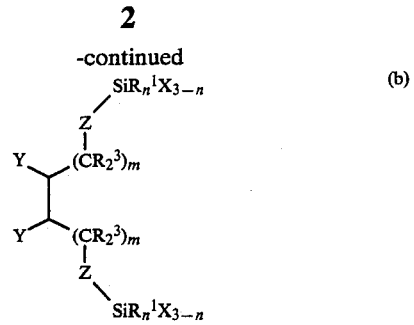

(b)

where
$X = Cl$, $Br$ or $-OR^2$;
$Y = -NR_2^4$, a nitrogen-containing aryl radical, $-PR_2^4$, $AsR_2^4$, $-SR^4$ or $-SH$;
$Z =$ zero, arylene or phenylene (optionally ortho-, meta- or para-substituted),
$R^1 = C_1$ to $C_5$-alkyl;
$R^2 = C_1$ to $C_5$-alkyl or $-C_6H_5$;
$R^3 = -H$ or $C_1$ to $C_3$-alkyl;
$R^4 = C_1$ to $C_6$-alkyl, $C_5$ or $C_6$-cycloalkyl or $-C_6H_5$ or $-CH_2C_6H_5$, which are optionally substituted by halogen, methoxy, ethoxy or $C_1$ to $C_3$-alkyl groups;
$n = 0$ or $1$ or $2$;
$m = 2$ to $6$, preferably $2$ to $4$.

In addition, the supported catalyst of the invention may optionally and preferably have the features that
(a) the chelate-forming organosilicon compound in the supported catalyst, is bound, as the polyfunctional coupling agent, on the one hand to the support material and on the other hand alternately to the noble-metal compound and to a non-noble-metal compound from sub-group 6 or 8 of the Periodic Table;
(b) the supported catalyst additionally contains, as promoters, non-noble-metal compounds from main groups 1 to 3 or sub-groups 4 to 6 or 8 of the Periodic Table;
(c) the supported catalyst contains an inorganic oxidic support material or an activated charcoal support, whose residual active hydroxyl groups have been deactivated by esterification or etherification;
(d) the supported catalyst contains in total 0.01 to 50% by weight, preferably 0.1 to 20% by weight, of noble-metal compound, coupling agent and, where appropriate, non-noble-metal compound.

Suitable catalyst supports are preferably inorganic oxides, such as, for example, $SiO_2$, $Al_2O_3$, $MgO$, $TiO_2$, $La_2O_3$, $ZrO_2$, zeolite, clay, $NiO$, $Cr_2O_3$, $WO_3$ or corresponding mixed oxides, but also activated charcoal, which BET surface areas of 1–1000 m²/g, preferably 30–400 m²/g, and must always also contain active OH groups. These OH groups react with the functional group(s) X of the coupling agent to form oxygen bridges between the support and the coupling agent.

Again as in German Offenlegungsschriften 3,440,646 and 3,511,048, the promoters of main group 5 or 6 are chemically bonded in the coupling agents employed according to the invention They themselves form a functional group which is chelated by the noble-metal compounds of group VIII and, where appropriate, non-noble-metal compounds of sub-group 6 or 8.

It is an advantage that the promoters of main group 5 or 6 of the Periodic Table of the Elements which are necessary to increase the catalyst activity and selectivity form a functional group Y in the polyfunctional coupling agents and can thus be immobilized to the maximum concentration, which is determined by the number of OH groups on the support surface. Separation and recycling of these, for example, organonitrogen or organophosphorus promoters is therefore superfluous.

The supported catalyst of the invention for the preparation of monocarboxylic anhydrides has higher selectivities and longer service lives, particularly in the case of long-term use, than the supported catalysts of German Offenlegungsschrift 3,440,646.

A further advantage of the invention is that it is possible to chemically immobilize noble-metal chelates on the support material surfaces In addition, the modified noble-metal chelate compounds and, where appropriate, non-noble-metal chelate compounds applied to the support material exhibit even higher melting points (240–270° C.) than the complexes described in German Offenlegungsschriften 3,440,646 and 3,511,048, which results in higher thermal stability of the catalysts and in an increase in the range of use of from 20° to 50° C.

The supported catalyst of the invention is used, in particular, for the preparation of acetic anhydride from methyl acetate or dimethyl ether in the presence of methyl iodide or methyl bromide as reaction promoter. It is also possible to employ HI, HBr or generally RI or RBr as reaction promoter, where R represents an alkyl radical having 1–4 carbon atoms.

In the general formulae for the organosilicon compounds suitable as coupling agents (spacers), X preferably denotes $-OR^2$ and in particular methoxy or ethoxy. If n is not zero, $R^1$ denotes an unbranched alkyl radical, in particular methyl, ethyl or propyl.

The support materials have already been mentioned; suitable mixed oxides are, for example $Cr_2O_3-Al_2O_3$, $WO_3-Al_2O_3$, $MgO-Al_2O_3$, $SiO_2-Al_2O_3$ or $ZrO_2-Al_2O_3$. The supported catalyst preferably contains 0.05 to 5% by weight of noble metal.

Noble-metal compounds which can be employed in the preparation of the supported catalyst are, for example the following compounds:

Rhodium:
$RhCl_3$, $RhCl_3$, 3 $H_2O$, $RhBr_3$, $RhI_3$, $Rh(NO_3)_3$, $Rh_2(CO)_4Cl_2$, $Rh_2(CO)_4Br_2$, $Rh(CO)_4I_2$, $[P(C_6H_5)_3]_3RhCl$, $[P(C_6H_5)_3]_2Rh(CO)Cl$, $Rh_6(CO)_{16}$, $Rh_4(CO)_{12}$, $Rh_2(O_2CCH_3)_4$, $[RhCl(C_3H_{12})]_2$;

Iridium:
$IrCl_3$, $[Ir(CO)_3Cl]_2$, $Ir[P(C_6H_5)_3]_2(CO)Cl$, $Ir_4(CO)_{12}$, $[IrCl(C_3H_{12})]_2$, $Cl(CO)_2Irpyr$ (pyr=$C_6H_5N$);

Palladium:
$PdCl_2$, $PdBr_2$, $PdI_2$, $(CH_3CO_2)_2Pd[P(C_6H_5)_3]_2$, $PdCl_2[P(C_6H_5)_3]_2$, $Pd(O_2CCH_3)_2$, $PdCl_2(C_8H_{12})$, $(C_6H_5CN)_2PdCl_2$;

Ruthenium:
$RuCl_3$, $Ru_3(CO)_{12}$, $RuCl_2[P(C_6H_5)_3]_3$, $RuCl_2(CO)_2[P(C_6H_5)_3]_2$, $[RuCl_2(CO)_3]_2$.

Suitable non-noble-metal compounds from sub-group 6 or 8, in particular Cr, Ni, but also W, Fe or Co, which likewise react with the chelating agents are furthermore the following, for example:

Chromium:
$Cr(CO)_6$, $CrCl_3$, $C_7H_8Cr(CO)_3$.

Nickel:
$Ni(CO)_4$, $[P(C_6H_5)_3]_2Ni(CO)_2$, $NiCl_2$, $Ni(C_8H_{12})_2$.

Non-noble-metal compounds which can be employed from main groups 1 to 3 or sub-groups 4 to 6 or 8 of the Periodic Table, preferably of Li, Na, Mg, Ca, Al, Ti, Zr, V, Cr, W, Fe, Co, or Ni, are, for example, hydroxides, carbonates, carbonyls, hydrides, halides and other salts. These compounds of non-noble metals may be additionally applied to the catalyst support by impregnation, for example as a solution.

In order to prepare the supported catalyst of the invention, it is first necessary to prepare the polyfunctional coupling agent, i.e. the chelate-forming organosilicon compound, containing the functional groups Y. This can be prepared analogously to literature references. In general, one of the noble-metal compounds mentioned from group VIII and, where appropriate, one of the non-noble-metal compounds mentioned from sub-group 6 or 8 is then connected, in solution, with the coupling agent, chelate compounds being produced which are suitable, due to their organosilicon function, for chemical immobilization.

This is followed by reactive adduction of the noble-metal-containing chelate with the OH groups of the support material with elimination of a group X as XH (for example HCl, HBr or $HOR^2$). This is accomplished by heating the components suspended in a non-polar solvent at the reflux temperature for 24 to 100 hours.

All further details on the syntheses can be found in the description of the catalyst preparation.

The mixing ratio of carboxylic acid ester or dialkyl ether and iodine (compound) or bromine (compound) in the reaction zone may vary within broad limits. In general, the amount of carboxylic acid ester and/or dialkyl ether is 1 to 500 moles, preferably 1 to 100 moles, per mole of iodine (compound) or bromine (compound). The temperature of the reaction zone is selected so that the reaction mixture is gaseous at any desired conversion. The temperature is preferably selected between 150° and 250° C. The preferred pressure is between 5 and 30 bar.

The residence time of the reaction mixture on the solid supported catalyst is 1 to 1000 seconds, preferably 1 to 180 seconds. The reaction can take place in a flow tube, which is preferably arranged vertically and packed with supported catalyst, or alternatively in a stirred or shaken autoclave containing the supported catalyst. The carbonylation is generally carried out under virtually anhydrous conditions; however, the presence of small amounts of water, as occur in the commercially available starting materials, is permissible, but should not exceed 1 mole %, based on the starting materials. Neither is the carbonylation impaired by small amounts of methanol in the starting materials. Hydrogen, which may be present in small amounts in commercially available carbon monoxide, also has little effect.

The reaction mixture flowing out of the carbonylation zone is gaseous and contains carbon monoxide, methyl iodide, acetic anhydride, unreacted methyl acetate or dimethyl ether and possibly small amounts of acetic acid.

The gaseous reaction mixture is cooled, acetic anhydride and possibly acetic acid condense out, and the non-condensed substances, such as CO, methyl iodide, methyl acetate or dimethyl ether, are fed back into the reaction zone. The amounts of ester or ether and CO which have reacted are continuously replaced.

Simple separation of the anhydrides by cooling the reaction mixture flowing out and recycling the non-condensible gases, as in the known processes mentioned, represents an essential advantage since this can take place without complicated separation operations. The supported catalyst is not contaminated and remains in the reaction zone, which considerably simplifies the overall course of the process.

EXAMPLES

Description of the catalyst preparation

In all cases, the catalyst support was previously dried for 10 hours at 200° C. and 0.1 mbar for activation. After application of the metal component, the catalysts were heated at the boiling point for 8 hours with chlorotrimethylsilane and subsequently dried at 0.1 mbar and 100° C. All the syntheses were carried out in an argon atmosphere with exclusion of atmospheric oxygen and water. All the solvents used were previously dried over molecular sieve 4 A or, if possible, dried using sodium benzophenone.

Stirred autoclave experiments

A 0.25 liter capacity stirred autoclave made from corrosion-free stainless steel (Hastelloy C), provided with the necessary inlet and outlet lines and containing a rotatable catalyst basket, is used.

The carboxylic acid esters or dialkyl ethers are reacted in the gas phase with CO gas in the presence of the agitated, solid supported catalyst. The supported catalyst is located in the rotatable catalyst basket, which simultaneously ensures thorough mixing of the gases.

The autoclave is charged with 2.5 ml of a liquid mixture comprising 20 parts by volume of methyl iodide and 80 parts by volume of ester or ether and is heated to the reaction temperature. The carbonylation is initiated by injecting carbon monoxide. The CO pressure is kept constant by regular re-injection.

The details on the experimental procedures can be seen from the examples.

In the Examples below $\phi$ denotes $C_6H_5$—.

EXAMPLE 1

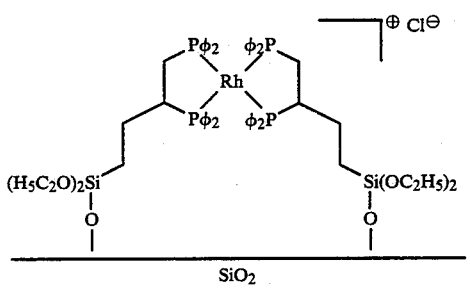

150 ml of a solution of 722 mg of complex 4 in toluene were added to 62.9 g of activated silicon dioxide pellets measuring ⅛"×⅛" (95% $SiO_2$) and having a BET internal surface area of 68 $m^2/g$ and a pore volume of 0.43 ml/g. The yellow suspension was refluxed for 24 hours, the solvent becoming completely colorless. After the toluene had been removed under reduced pressure, the catalyst was dried at 0.1 mbar and 150° C. for 6 hours and subsequently extracted for 24 hours in a Soxhlet apparatus with benzene. After extraction, no rhodium was detected in the benzene.

Characterization: pale yellow pellets
Rh content: 0.09% by weight

Synthetic route for rhodium complex 4 1,2-Dichloro-4-(triethoxysilyl)butane (2):

0.5 mol of tetraethoxysilane are added dropwise to 0.1 mol of 1-butenylmagnesium bromide (1) in 100 ml of tetrahydrofuran, and the mixture was refluxed for 5 hours. The suspension obtained is subsequently filtered, and the solvent is stripped off. The residue is taken up in dichloromethane, and chlorine is passed in at 0° C. until the solution becomes a pale yellow color. After the solvent has been stripped off and after subsequent vacuum distillation, 2 is obtained in a yield of 64%.

1,2-Bis(diphenylphosphino)-4-(triethoxysilyl)butane (3):

3 is synthesized by reacting twice the molar amount of sodium diphenylphosphide in dioxane with 2, dissolved in tetrahydrofuran, at room temperature [analogous to 1,2-bis(diphenylphosphino)ethane; see K. Issleib and D. -W. Müller, Chem. Ber. 92, 3175 (1959)]. Yield 72%.

[1,2-Bis(diphenylphosphino)-4-(triethoxysilyl)-butane]rhodium(I) chloride (4):

4 mmol of 3, dissolved in benzene, are added dropwise with stirring to a solution of 1 mmol of dichlorotetracarbonyldirhodium in benzene. Stripping off the solvent and recrystallization from hexane gas gives analytically pure complex 4. Yield 94%. Cf. the synthesis of [1,2-bis(diphenylphosphino)ethane]rhodium(I) chloride; A. Sacco et al., J. Chem. Soc. (London), 3274 (1964).

2 ml (1.86 g) of methyl acetate, 0.5 ml (1.14 g) of methyl iodide and 7.2 g of the catalyst are reacted in the autoclave with carbon monoxide at a CO pressure of 15 bar and at 180° C. After a reaction time of 1 hour, a catalyst performance of 19.7 g $Ac_2O$/g of Rh per hour is obtained, at a selectivity of 95%.

A steel tube 20 mm in diameter and 400 mm in length is arranged vertically as a flow tube and packed with 50.6 g of the catalyst. At a pressure of 12 bar and a temperature of 180° C., 8 l (s.t.p.) per hour CO (l (s.t.p.)=liters, measured at 1.013 bar and 0° C.), and an evaporated mixture (12.8 ml of liquid) of methyl iodide and methyl acetate (molar ratio 1:4) ar passed through the flow tube.

The reaction mixture flowing out is analyzed on-line by gas chromatography. A space-time yield of 12.5 g of $Ac_2O$/g of Rh per hour is obtained here at a selectivity of 97%.

The carbonylation was carried out for 280 hours under these reaction conditions, the supported catalyst employed exhibiting no loss in activity.

EXAMPLE 2

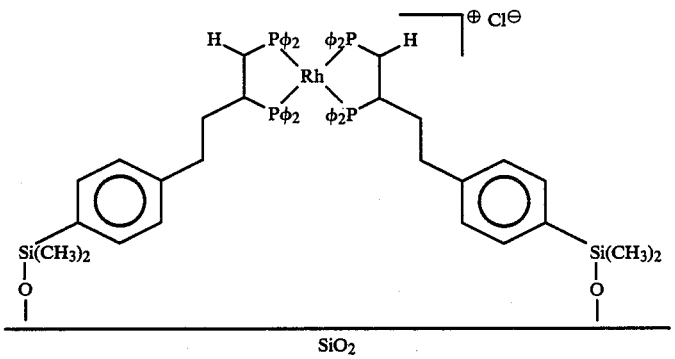

50 ml of a solution of 133 mg of complex 9 in toluene were added to 12.7 g of activated silicon dioxide pellets measuring ⅛"×⅛" (95% SiO₂) and having a BET internal surface area of 68 m²/g and a pore volume of 0.43 ml/g. The yellow suspension was refluxed for 24 hours, the solvent becoming completely colorless. After the toluene had been stripped off under reduced pressure, the catalyst was dried at 0.1 mbar and 150° C. for 6 hours and subsequently extracted for 24 hours in Soxhlet apparatus with benzene. After the extraction, no rhodium was detected in the benzene.

Characterization: pale yellow pellets
Rh content: 0.08% by weight
Synthetic route for rhodium complex 9 1,2-Dichloro-4-(4-chlorophenyl)butane (6):

6 can be synthesized by reacting 4-(4-chlorophenyl)-butene (5) with chlorine at 0° C. in dichloromethane. Yield 93%.

1,2-Bis(diphenylphosphino)-4-(4-chlorophenyl)butane (7):

7 is synthesized by reacting twice the molar amount of sodium diphenylphosphide in dioxane with 6, dissolved in tetrahydrofuran, at room temperature in a yield of 82% [analogous to 1,2-bis(diphenylphosphino)ethane; see K. Issleib and D.-W. Müller, Chem. Ber. 92, 3175 (1959)].

1,2-Bis(diphenylphosphino)-4-[4-dimethylethoxysilyl)phenyl]butane (8):

0.05 mol of 7 are converted in tetrahydrofuran into the arylmagnesium chloride compound [see R. D. Rieke and S. E. Bales, J. Am. Chem. Soc. 96, 1775 (1974); J. P. Collmann et al., J. Am. Chem. Soc. 105, 7288 (1983). 0.25 mol of diethoxydimethylsilane is subsequently added dropwise with stirring and ice cooling, and the mixture is allowed to warm to room temperature and finally refluxed for 5 hours. The reaction mixture is filtered; the solvent and excess diethoxydimethylsilane are stripped off in vacuo. The oily residue is crystallized from hexane, and 8 is obtained in a yield of 68%.

[1,2-Bis(diphenylphosphino)-4-[4-dimethylethoxysilyl)phenyl]butane]rhodium(I) chloride (9):

4 mmol of 8, dissolved in benzene, are added dropwise with stirring to a solution of 1 mmol of dichlorotetracarbonyldirhodium in benzene. Stripping off the solvent and recrystallization from hexane gives analytically pure complex 9. Yield 95%. Cf. the synthesis of [1,2-bis(diphenylphosphino)ethane]rhodium(I) chloride; A. Sacco et al., J. Chem. Soc. (London), 3274 (1964).

2 ml (1.86 g) of methyl acetate, 0.5 ml (1.14 g) methyl iodide and 7.9 g of the catalyst are reacted in the autoclave with carbon monoxide at a CO pressure of 15 bar and 180° C. After a reaction time of 1 hour, a catalyst performance of 18.8 g of Ac₂O/g of Rh per hour is obtained, at a selectivity of 96%.

EXAMPLE 3

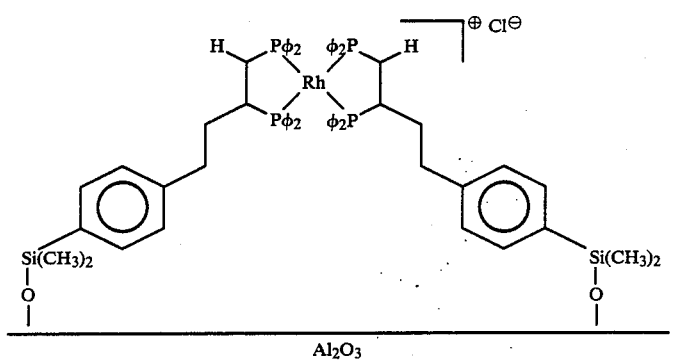

50 ml of a solution of 156 mg of complex 9 in toluene were added to 11.7 g of activated aluminum oxide beads (99% Al₂O₃) having a diameter of 3 mm, a BET internal surface area of 125 m²/g and a pore volume of 0.9 ml/g. The yellow suspension was refluxed for 24 hours, the solution becoming completely colorless. After the toluene had been stripped off under reduced pressure, the catalyst was dried at 0.1 mbar and 150° C. for 6 hours, and subsequently extracted for 24 hours in a Soxhlet apparatus with benzene. After the extraction, no rhodium was detected in the benzene.

Characterization: pale yellow beads
Rh content: 0.1% by weight 2 ml (1.86 g) of methyl acetate, 0.5 ml (1.14 g) of methyl iodide and 6.5 g of the catalyst are reacted in the autoclave with carbon monoxide at a CO pressure of 15 bar and at 180° C. After a reaction time of 1 hour, a catalyst performance of 41.0 g of Ac2O/g of Rh per hour is obtained, at a selectivity of 89%.

We claim:

1. A supported catalyst for the preparation of a monocarboxylic anhydride by carbonylation of the appropriate ester or ether, where, in the supported catalyst, an organosilicon compound containing alkoxy or halogen groups and containing organonitrogen, organophosphorus, organoarsenic, organosulfur or mercapto groups, is bonded, as a polyfunctional coupling agent, on the one hand to a support material and on the other hand to a noble-metal compound from group VIII of the Periodic Table of the Elements, wherein, the coupling agent is a chelate-forming organosilicon compound of the formula

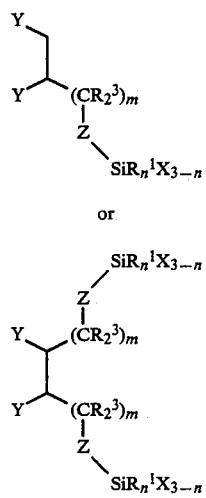

where
X = —Cl, —Br or —OR$^2$;
Y = —NR$_2^4$, a nitrogen-containing aryl radical, —PR$_2^4$, AsR$_2^4$, —SR$^4$ or —SH;
Z = zero, arylene or phenylene;
R$^1$ = C$_1$ to C$_5$-alkyl;
R$^2$ = C$_1$ to C$_5$-alkyl or —C$_6$H$_5$;
R$^3$ = —H or C$_1$ to C$_3$-alkyl;
R$^4$ = C$_1$ to C$_6$-alkyl, C$_5$ or C$_6$-cycloalkyl or —C$_6$H$_5$ or —CH$_2$C$_6$H$_5$;
n = 0 or 1 or 2;
m = 2 to 6.

2. A supported catalyst as claimed in claim 1, wherein the chelate-forming organosilicon compound is bonded, as the polyfunctional coupling agent, on the one hand to the support material and on the other hand alternately to the nobel-metal compound and to a non-noble-metal compound from the sub-group 6 or 8 of the Periodic Table.

3. A supported catalyst as claimed in claim 1, additionally containing as promoters, non-noble-metal compounds from main groups 1 to 3 or sub-groups 4 to 6 or 8 of the Periodic Table.

4. A supported catalyst as claimed in claim 1, containing an inorganic oxidic support material or an activated charcoal support, whose residual active hydroxyl groups have been deactivated by esterification or etherification.

5. A supported catalyst as claimed in claim 1, containing a total of 0.01 to 50% by weight of noble-metal compound, coupling agent and optionally non-noble-metal compound.

6. A supported catalyst as claimed in claim 1, having the formula

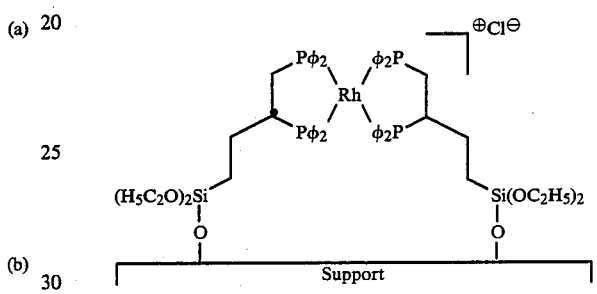

7. A supported catalyst as claimed in claim 1, having the formula

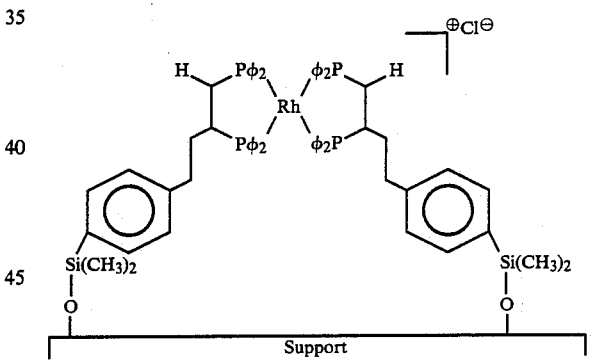

8. A supported catalyst as claimed in claim 1, wherein the substituents R$^4$ are themselves substituted by halogen, methoxy, ethoxy or C$_1$ to C$_3$-alkyl groups.

9. A supported catalyst as claimed in claim 1, wherein substituent Z denotes ortho-, meta- or para-substituted phenylene.

* * * * *

UNITED STATES PATENT AND TRADEMARK OFFICE
CERTIFICATE OF CORRECTION

PATENT NO. : 4,965,234

DATED : October 23, 1990

INVENTOR(S) : Luft et al

It is certified that error appears in the above-identified patent and that said Letters Patent is hereby corrected as shown below:

On the title page item [73] Assignee: change "Hoechst Aktiengesellschaft, Hurth, Fed. Rep. of Germany" to read --Hoechst Aktiengesellschaft, Frankfurt/Main 80, Germany--.

Signed and Sealed this

Eighteenth Day of February, 1992

Attest:

HARRY F. MANBECK, JR.

*Attesting Officer*      *Commissioner of Patents and Trademarks*